(12) United States Patent
Nonaka et al.

(10) Patent No.: US 9,848,831 B2
(45) Date of Patent: Dec. 26, 2017

(54) APPARATUS FOR DETERMINING RESPIRATORY CONDITION

(71) Applicants: NIHON KOHDEN CORPORATION, Tokyo (JP); National University Corporation Chiba University, Chiba (JP)

(72) Inventors: Yukio Nonaka, Tokyo (JP); Shiroh Isono, Chiba (JP); Tsuyoshi Shimizu, Tokyo (JP)

(73) Assignees: NIHON KOHDEN CORPORATION, Tokyo (JP); NATIONAL UNIVERSITY CORPORATION CHIBA UNIVERSITY, Chiba (JP)

( * ) Notice: Subject to any disclaimer, the term of this patent is extended or adjusted under 35 U.S.C. 154(b) by 907 days.

(21) Appl. No.: 13/901,135

(22) Filed: May 23, 2013

(65) Prior Publication Data
US 2013/0324877 A1    Dec. 5, 2013

(30) Foreign Application Priority Data

May 30, 2012    (JP) ................................ 2012-123248

(51) Int. Cl.
*A61B 5/087*    (2006.01)
*A61B 5/00*    (2006.01)
(Continued)

(52) U.S. Cl.
CPC ............. *A61B 5/742* (2013.01); *A61B 5/087* (2013.01); *A61B 5/0826* (2013.01);
(Continued)

(58) Field of Classification Search
CPC ..... A61B 5/0826; A61B 5/087; A61B 5/4818; A61B 5/7239; A61B 5/742;
(Continued)

(56) References Cited

U.S. PATENT DOCUMENTS

| 5,060,656 A | 10/1991 | Howard |
| 5,117,674 A | 6/1992 | Howard |

(Continued)

FOREIGN PATENT DOCUMENTS

| CN | 101340869 A | 1/2009 |
| CN | 101897589 A | 12/2010 |

(Continued)

OTHER PUBLICATIONS

"Section 2.6: Second Derivative and Concavity." Business Calculus. 2015.*

(Continued)

Primary Examiner — Jacqueline Cheng
Assistant Examiner — Jairo Portillo
(74) Attorney, Agent, or Firm — Kenealy Vaidya LLP

(57) ABSTRACT

An apparatus for determining a respiratory condition, the apparatus includes: a signal acquirer which is configured to acquire a signal waveform corresponding to a respiratory flow of a subject; a differential calculator which is configured to acquire a differential waveform which is obtained by performing differentiation of the signal waveform; and a first determiner which is configured to determine that inspiratory flow limitation occurs in the subject, when the differential waveform satisfies a predetermined condition in a portion of the signal waveform, which corresponds to inspiration of the subject.

6 Claims, 3 Drawing Sheets

(51) Int. Cl.
*A61B 5/08* (2006.01)
*A61M 16/00* (2006.01)
*A61M 16/06* (2006.01)

(52) U.S. Cl.
CPC ....... *A61B 5/7239* (2013.01); *A61M 16/0051* (2013.01); *A61M 16/0672* (2014.02); *A61B 5/4818* (2013.01); *A61M 2016/0027* (2013.01); *A61M 2205/502* (2013.01)

(58) Field of Classification Search
CPC .......... A61M 16/0051; A61M 16/0672; A61M 2016/0027; A61M 2205/502
See application file for complete search history.

(56) References Cited

U.S. PATENT DOCUMENTS

| | | | |
|---|---|---|---|
| 5,363,857 A | 11/1994 | Howard | |
| 5,540,733 A * | 7/1996 | Testerman | A61B 5/1135 600/529 |
| 5,803,066 A * | 9/1998 | Rapoport | A61B 5/0002 128/204.21 |
| 6,368,287 B1 * | 4/2002 | Hadas | A61B 5/0878 600/529 |
| 7,325,545 B2 | 2/2008 | Dellaca' et al. | |
| 7,722,546 B2 * | 5/2010 | Madaus | A61B 5/087 600/529 |
| 2003/0055346 A1 * | 3/2003 | Rapoport | A61B 5/0002 600/489 |
| 2003/0100843 A1 * | 5/2003 | Hoffman | A61B 5/0809 600/538 |
| 2004/0054295 A1 * | 3/2004 | Ramseth | G06F 19/3412 600/509 |
| 2005/0256420 A1 * | 11/2005 | Norman | A61B 5/087 600/533 |
| 2005/0268866 A1 | 12/2005 | Finkbeiner et al. | |
| 2006/0241509 A1 * | 10/2006 | Badr | A61B 5/085 600/533 |
| 2006/0249149 A1 | 11/2006 | Meier et al. | |
| 2008/0097234 A1 * | 4/2008 | Nicolazzi | A61B 5/087 600/538 |
| 2008/0243017 A1 * | 10/2008 | Moussavi | A61B 5/087 600/532 |
| 2008/0308112 A1 | 12/2008 | Aarts | |
| 2010/0258124 A1 | 10/2010 | Madaus et al. | |
| 2010/0275921 A1 * | 11/2010 | Schindhelm | A61B 5/08 128/204.23 |
| 2011/0203588 A1 * | 8/2011 | Armitstead | A61M 16/0051 128/204.21 |
| 2011/0230779 A1 * | 9/2011 | Titchener | A61B 5/087 600/538 |
| 2014/0290656 A1 | 10/2014 | Madaus et al. | |

FOREIGN PATENT DOCUMENTS

| | | |
|---|---|---|
| JP | 7-67856 A | 3/1995 |
| JP | 2006-502774 A | 1/2006 |
| JP | 2006-520227 A | 9/2006 |
| JP | 4588461 B2 | 12/2010 |
| WO | WO 2010021556 A1 * | 2/2010 ............. A61B 5/087 |

OTHER PUBLICATIONS

"Concavity and Inflection Points." Calculus: early transcentals. 2013.*
Chinese Office Action for the related Chinese Patent Application No. 201310196223.5 dated Mar. 3, 2016.
Japanese Office Action for the related Japanese Patent Application No. 2012-123248 dated Jan. 19, 2016.
Japanese Office Action for the related Japanese Patent Application No. 2012-123248 dated Aug. 23, 2016.
Chinese Office Action for the related Chinese Patent Application No. 201310196223.5 dated Aug. 15, 2016.
The extended European Search Report for the related European Patent Application No. 13169071.1 dated Sep. 4, 2013.

* cited by examiner

APPARATUS FOR DETERMINING RESPIRATORY CONDITION

CROSS-REFERENCE TO RELATED APPLICATION(S)

This application is based upon and claims the benefit of priority from prior Japanese patent application No. 2012-123248, filed on May 30, 2012, the entire contents of which are incorporated herein by reference.

BACKGROUND

The presently disclosed subject matter relates to an apparatus for determining the presence of inspiratory flow limitation which is known as a symptom of a sleep disorder, and the kind of the apnea/hypopnea condition based on the respiration of the subject.

As an apparatus of this kind, there is an apparatus in which a signal waveform corresponding to the respiratory condition of the subject is acquired overnight, and the presence of inspiratory flow limitation is visually determined from the shape of the signal waveform (for example, see U.S. Pat. No. 7,325,545).

As disclosed in Japanese Patent No. 4,588,461, a strip-like strain gauge is wound around the chest or the abdomen to detect a motion of the portion, and a result of the detection is collated with a signal waveform corresponding to the respiratory condition, to detect an apnea/hypopnea condition during sleep and to determine the kind thereof. Apnea/hypopnea conditions are roughly classified into two categories, namely, obstructive apnea/hypopnea in which a respiratory effort is continued in an airway obstruction condition, and central apnea/hypopnea in which a respiratory effort itself stops to cease the ventilation. The inspiratory flow limitation is used as an index indicating the obstructive apnea/hypopnea condition.

Attachments of various kinds of sensors for detecting an apnea/hypopnea condition during sleep to the body impose a large burden on the subject. On the other hand, the work of visually determining the presence of inspiratory flow limitation from an enormous number of measurement signal waveforms that were obtained from the respiration of the subject by an overnight measurement, and determining the kind of the apnea/hypopnea condition constitutes a very large burden on the person performing the diagnosis. In the case of a determination based on visual observations, it is difficult to eliminate differences in the determination due to the subjectivity and experience of the observer.

SUMMARY

The presently disclosed subject matter may provide a technique in which the presence of inspiratory flow limitation during sleep, and the kind of the apnea/hypopnea condition can be determined correctly and easily while reducing the botheration and burden on the subject.

There is provided an apparatus for determining a respiratory condition, the apparatus comprising: a signal acquirer which is configured to acquire a signal waveform corresponding to a respiratory flow of a subject; a differential calculator which is configured to acquire a differential waveform which is obtained by performing differentiation of the signal waveform; and a first determiner which is configured to determine that inspiratory flow limitation occurs in the subject, when the differential waveform satisfies a predetermined condition in a portion of the signal waveform, which corresponds to inspiration of the subject.

The differential calculator may acquire a secondary differential waveform which is obtained by performing secondary differentiation of the signal waveform, as the differential waveform, and the first determiner may determine that the inspiratory flow limitation occurs in the subject, based on a time period during which an amplitude of the secondary differential waveform is smaller than a predetermined threshold.

The first determiner may determine that the inspiratory flow limitation occurs in the subject, based on a time period during which the amplitude of the secondary differential waveform has a negative value.

The first determiner may identify start and end phases of the inspiration of the subject based on a gradient of the signal waveform, and may perform the determination based on the time period in a region excluding the start and end phases.

The apparatus may further comprise: a second determiner which is configured to determine an apnea/hypopnea condition of the subject, based on an average value of an amplitude of the signal waveform in a predetermined past time period; and a third determiner which is configured to determine whether kind of the apnea/hypopnea condition is obstructive or central, based on a presence of the inspiratory flow limitation which is determined by the first determiner and the apnea/hypopnea condition which is determined by the second determiner.

The apparatus may further comprise: a display which is configured to display the signal waveform; and a display controller which is configured to cause at least one of an index indicating the presence of the inspiratory flow limitation which is determined by the first determiner, an index indicating the apnea/hypopnea condition which is determined by the second determiner, and an index indicating the kind of the apnea/hypopnea condition which is determined by the third determiner, to be displayed on the display together with the signal waveform.

The apparatus may further comprise: a pressure sensor which is configured to measure a respiratory pressure of the subject, and the signal acquirer may acquire the signal waveform based on a measurement waveform corresponding to the respiratory pressure which is output from the pressure sensor.

The signal acquirer may perform a square root correction on the measurement waveform to acquire the signal waveform.

The apparatus may further comprise: a nasal cannula which is to be attached to the subject, and the signal acquirer may acquire the signal waveform based on a respiratory pressure which is introduced through the nasal cannula.

DETAILED DESCRIPTION OF EXEMPLARY EMBODIMENTS

Hereinafter, an embodiment of the presently disclosed subject matter will be described in detail with reference to the accompanying drawings.

Figure 1:
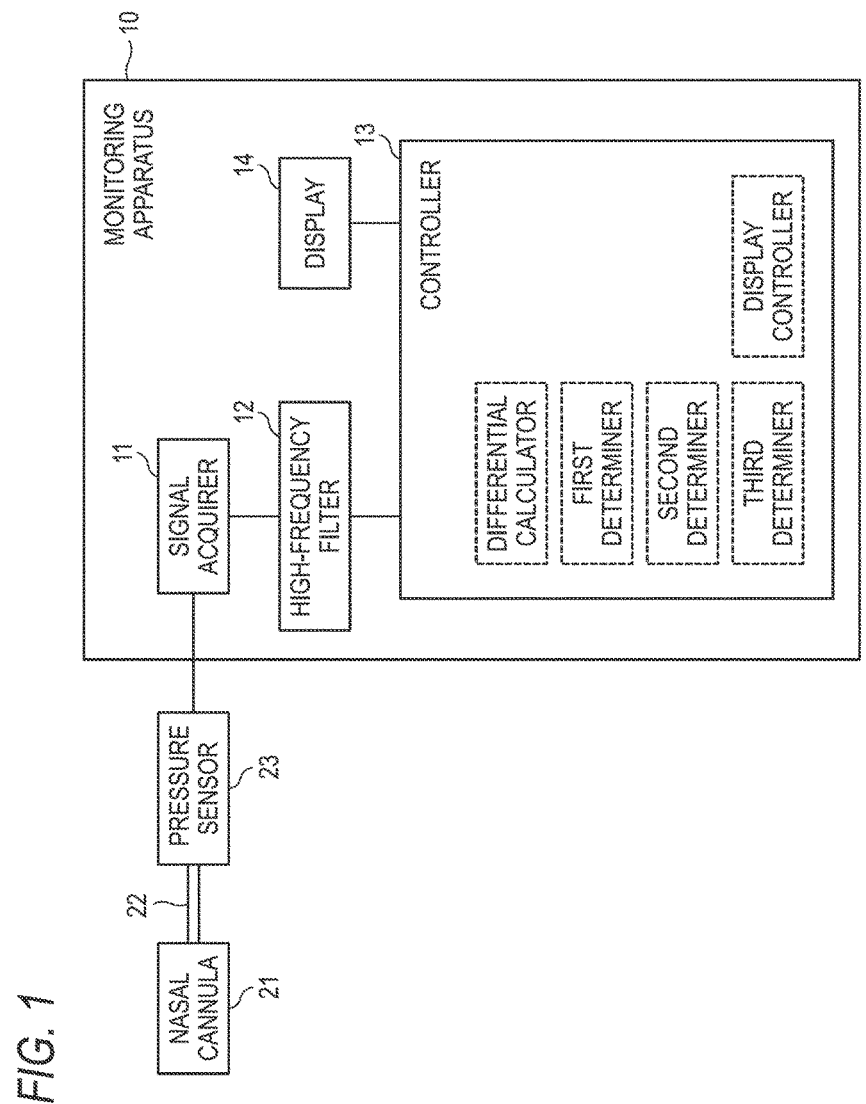
FIG. 1 is a functional block diagram showing the configuration of a monitoring apparatus of an embodiment of the presently disclosed subject matter.

FIG. 1 is a functional block diagram showing the configuration of a monitoring apparatus 10 which is an apparatus for determining the respiratory condition according to an embodiment of the presently disclosed subject matter. The monitoring apparatus 10 includes a signal acquirer 11, a high-frequency filter 12, a controller 13, and a display 14.

A nasal cannula 21 is a device in which a pair of pipe portions are to be inserted to the nostrils of the subject to guide the nasal respiratory gas of the subject to a pressure sensor 23 through a tube 22. The pressure sensor 23 is a sensor which measures a pressure change caused by respiration of the subject, and outputs a measurement signal having a waveform corresponding to the respiratory condition (respiratory pressure) of the subject (in following description, the signal is referred to merely as the measurement waveform).

Figure 2A:
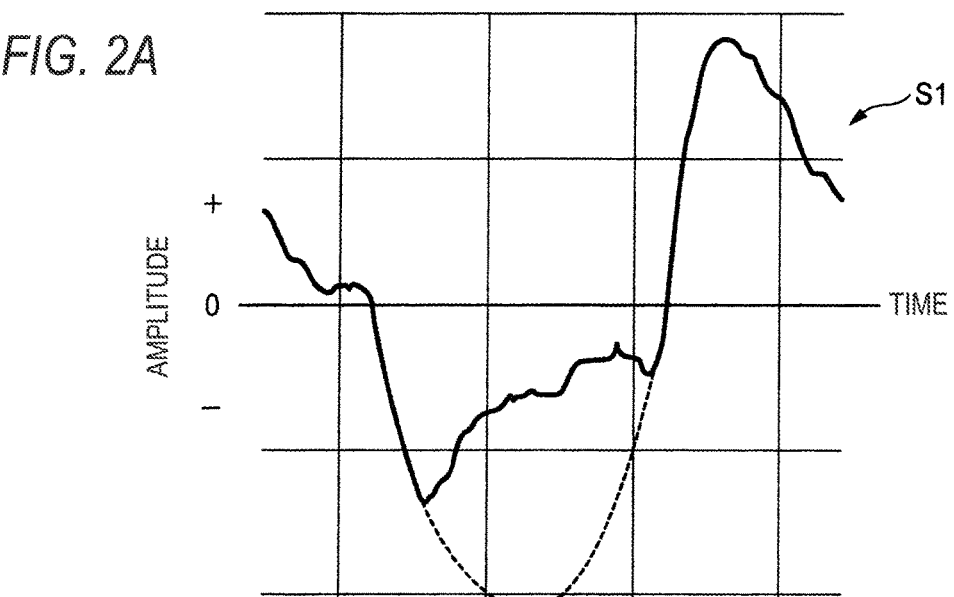
FIGS. 2A, 2B and 2C are views illustrating signal processing performed by the monitoring apparatus of FIG. 1.

Originally, it is preferable to determine the respiratory condition of the subject through measurement of the respiratory flow. However, such measurement requires a countermeasure for preventing the respiratory gas from leaking. By contrast, it is known that a good approximate value of the respiratory flow is obtained by multiplying the value of the respiratory pressure by a predetermined constant and then extracting the square root. This calculation process is referred to as the square root correction. In the embodiment, in order to more facilitate the measurement, the signal acquirer 11 acquires a signal waveform S1 by performing the square root correction on the measurement waveform supplied from the pressure sensor 23. An example of the acquired signal waveform S1 is shown in FIG. 2A.

Figure 2B:
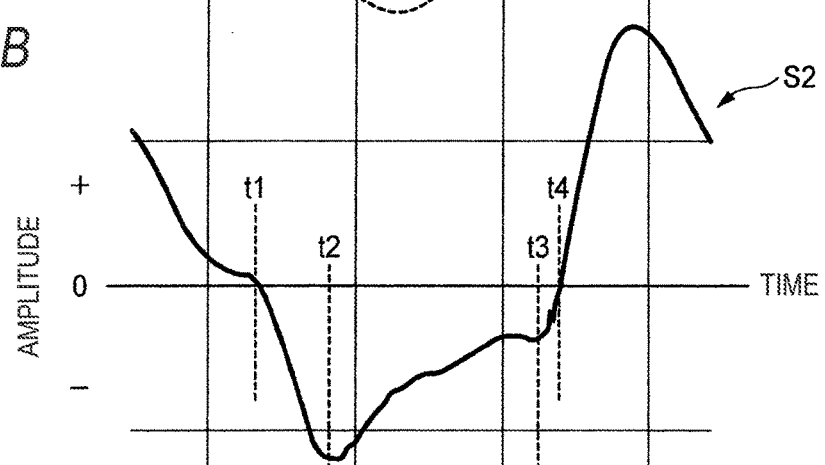

The high-frequency filter 12 is an electrical filter which removes high-frequency components of the signal waveform S1 which is acquired by the signal acquirer 11 by means of the square root correction. When components which are higher in frequency than a predetermined frequency are removed away, the signal waveform is smoothed, and the correctness of the calculation process which will be described later is improved. FIG. 2B shows a signal waveform S2 from which high-frequency components contained in the signal waveform S1 of FIG. 2A are removed.

The inspiratory flow limitation is a phenomenon which is generated when the airway is obstructed during inspiration, and corresponds to a condition where, even when the patient wishes to breathe, the patient cannot breathe. As indicated by the broken line in FIG. 2A, in a normal condition, the respiratory pressure is lowered (the negative pressure is increased) as inspiration progresses. The signal waveform S1 in the figure shows a condition where inspiratory flow limitation occurs. As a result of inhibition of inspiration caused by airway obstruction, a phenomenon occurs in which the respiratory pressure is not lowered in a portion where the pressure should be originally lowered, but rather is raised.

In a measurement waveform of the respiratory pressure, therefore, an upward convex portion appears in a region which indicates inspiration, and in which a downwardly convex waveform should originally appear. In the monitoring apparatus 10 of the embodiment, the presence of the convex portion is detected from the acquired signal waveform S2, thereby determining whether inspiratory flow limitation presents or not.

The controller 13 extracts a region which corresponds to inspiration of the subject, from the signal waveform S2 shown in FIG. 2B. It is requested to extract a region in which the respiratory pressure is negative. Therefore, the controller 13 identifies a time t1 when the amplitude of the signal waveform S2 is changed from a positive value to a negative value, and a time t4 when the amplitude is changed from a negative value to a positive value.

Next, the controller 13 acquires the value of the gradient of the signal waveform S2 in the region from the time t1 to the time t4. In this case, the gradient value has the maximum value and then gradually decreases. The controller 13 identifies a time t2 when the gradient value is equal to or smaller than a predetermined rate with respect to the maximum value. Moreover, the controller 13 similarly acquires the value of the gradient of the signal waveform S2 in the region from the time t4 to the time t1. Also in this case, the gradient value has the maximum value and then gradually decreases. The controller 13 identifies a time t3 when the gradient value is equal to or smaller than a predetermined rate with respect to the maximum value. As a result, the zone between the times t1 and t2 is deemed as the start phase of inspiration, and that between the times t3 and t4 is deemed as the end phase of inspiration. In the embodiment, both the predetermined rates are 20% or less. This is because waveforms in the start and end phases of inspiration which are hardly distinguished from the waveform during normal inspiration are eliminated from the analysis target and a waveform region where inspiratory flow limitation notably occurs is extracted. At this time, the controller 13 functions as the differential calculator in the presently disclosed subject matter, and performs the above-described process based on the value of the gradient i.e., first differential of the signal waveform S2.

Figure 2C:
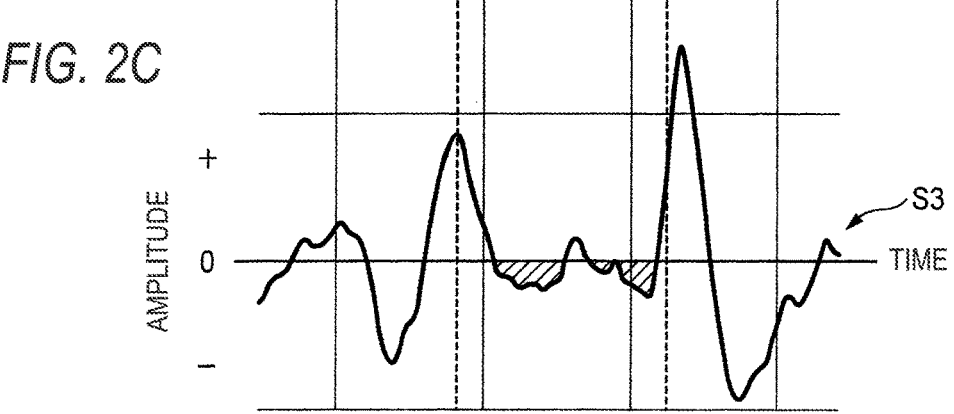

Moreover, the controller 13 which functions as the differential calculator acquires, as the differential waveform in the presently disclosed subject matter, a waveform that, as shown in FIG. 2C, is obtained by performing secondary differentiation of the signal waveform S2 from which high-frequency components are removed by the high-frequency filter 12. In the following description, the differential waveform is referred to as the secondary differential waveform S3.

Then, the controller 13 functions as the first determiner in the presently disclosed subject matter, and determines the occurrence of inspiratory flow limitation based on the time period which is indicated by hatching in FIG. 2C, and during which the amplitude of the secondary differential waveform S3 has a negative value. Specifically, a threshold is set to 0, and, when the rate of the time period during which the amplitude of the secondary differential waveform S3 has a negative value, with respect to the duration time (the zone between the times t1 and t4) of the portion which is in the signal waveform S2, and which corresponds to inspiration of the subject is equal to or larger than a predetermined value, it is determined that inspiratory flow limitation occurs. The threshold and the predetermined value can be adequately set by the user while considering individual difference in the subject and operation guidelines of the facility. When several thresholds are set in a stepwise manner, for example, the degree of intensity of inspiratory flow limitation can be determined.

In the embodiment, namely, the controller 13 which functions as the first determiner is configured so as to, when the differential waveform in the portion which is in the signal waveform S2, and which corresponds to inspiration of the subject satisfies predetermined conditions, determine that inspiratory flow limitation occurs in the subject. Therefore, the presence of inspiratory flow limitation can be uniformly determined without performing visual observation of the measurement waveform.

Moreover, the controller 13 which functions as the differential calculator acquires the secondary differential waveform S3 from the signal waveform S2, and the controller 13 which functions as the first determiner is configured so as to, when the rate of the time period during which the amplitude of the secondary differential waveform S3 has a negative value, with respect to the duration time of the portion which is in the signal waveform S2, and which corresponds to inspiration of the subject is equal to or larger than the predetermined value, determine that inspiratory flow limitation occurs. Consequently, it is possible to detect an upward convex portion which appears in a signal waveform corresponding to the respiratory pressure during inspiration, and which is large to some extent, and therefore it is possible to surely determine an occurrence of inspiratory flow limitation.

Moreover, the controller 13 which functions as the differential calculator acquires the gradient (primary differential value) of the signal waveform S2, and the controller 13 which functions as the first determiner is configured so as to identify the start and end phases of inspiration of the subject based on the gradient of the signal waveform, and acquire the time period during which the secondary differential waveform S3 has a negative value in the region excluding the start and end phases. While waveforms in the start and end phases of inspiration which are hardly distinguished from those of normal inspiration are eliminated from the analysis target, therefore, the presence of inspiratory flow limitation can be determined more surely.

Figure 3:
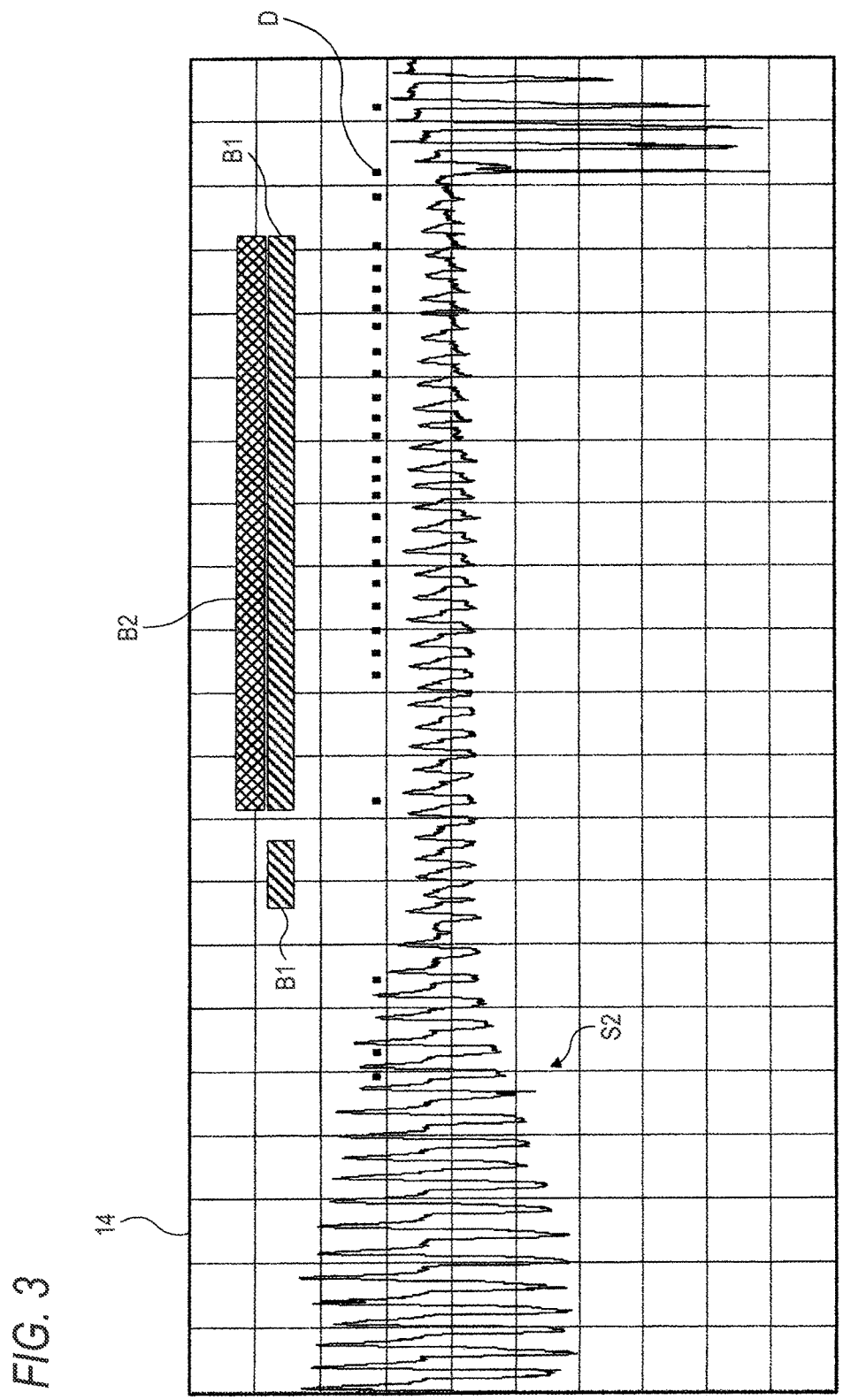
FIG. 3 is a view showing an example of a signal waveform displayed on a display of the monitoring apparatus of FIG. 1.

Furthermore, the controller 13 functions as the display controller in the presently disclosed subject matter, and, as shown in FIG. 3, causes the display 14 including a displaying device to display the signal waveform S2 in real time. The controller 13 which functions as the display controller causes the display 14 to display an index indicating the presence of inspiratory flow limitation which is detected through the above-described process. Specifically, a dot index D is displayed above the signal waveform S2 indicating inspiration which is determined that inspiratory flow limitation occurs. Therefore, a waveform in which inspiratory flow limitation occurs can be identified at a glance from an enormous number of respiration signal waveforms, and correct diagnosis which is not based on the subjectivity of the observer is enabled.

On the other hand, the controller 13 functions as the second determiner in the presently disclosed subject matter, and determines the apnea/hypopnea condition of the subject by means of a related-art technique based on the average value of the amplitude of the signal waveform S2 in a predetermined past time period. Here, the predetermined past time period is preferably set to, for example, a time period which is several minutes before the time when the analysis is to be performed.

Moreover, the controller 13 functions as the third determiner in the presently disclosed subject matter, and, based on the presence of inspiratory flow limitation which is determined as the first determiner, and that of the apnea/hypopnea condition which is determined as the second determiner, determines whether the apnea/hypopnea condition is obstructive or central. Specifically, when the occurrence of inspiratory flow limitation is detected in the signal waveform S2 which is determined to be in the apnea condition or the hypopnea condition, or in the signal waveform S2 which is in constant respiratory periods before and after of the signal waveform, the condition is determined to be obstructive. This is because the occurrence of inspiratory flow limitation means the existence of a respiratory effort. By contrast, when the occurrence of inspiratory flow limitation is not detected in the signal waveform S2 which is determined to be in the apnea condition or the hypopnea condition, or in the signal waveform S2 which is in the constant respiratory periods before and after of the signal waveform, it is determined that the condition is central apnea/hypopnea in which a respiratory effort does not exist.

The controller 13 which functions as the display controller causes the display 14 to display an index indicating the presence of the apnea/hypopnea condition which is determined as the second determiner. In the example shown in FIG. 3, a bar index B1 indicating the time zone where the condition is determined to be the hypopnea condition is displayed. Another bar index of a different color is displayed with respect to the time zone where the condition is determined to be the apnea condition. Therefore, a time zone in which the apnea/hypopnea condition occurs can be identified at a glance from an enormous number of respiration signal waveforms, and correct diagnosis which is not based on the subjectivity of the observer is enabled.

The controller 13 which functions as the display controller causes the display 14 to display an index indicating the kind of the apnea/hypopnea condition which is determined as the third determiner. In the example shown in FIG. 3, a bar index B2 indicating the apnea condition is displayed in the time zone where the condition is determined to be the hypopnea condition and inspiratory flow limitation occurs.

The embodiment is configured so that the bar index B2 is displayed in a place where the condition is determined to be the obstructive apnea/hypopnea condition. Because of this, the bar index B2 indicating the apnea condition is not displayed in the time zone where the condition is determined to be the hypopnea condition and inspiratory flow limitation is not detected.

In the embodiment, the bar index B2 is displayed for the obstructive apnea/hypopnea condition, and not displayed for the central apnea/hypopnea condition. Therefore, the kind of the apnea/hypopnea condition can be identified at a glance, and correct diagnosis which is not based on the subjectivity of the observer is enabled.

The diagnosis through the above-described series of processes can be performed simply by measuring the respiratory pressure of the subject. It is not necessary to attach various kinds of sensors to the body, and therefore botheration and pain which may be felt by the subject can be reduced. In the embodiment, particularly, only the nasal cannula which is small in size, and which is relatively light in weight is attached to the subject, and therefore interference with sleep can be suppressed.

The above-described functions of the controller 13, i.e., those as the differential calculator, the first determiner, the second determiner, the third determiner, and the display controller can be realized by the operation of hardware such as circuit devices constituting the controller 13, that of software such as programs stored in an arithmetic device, or a combination of these operations.

The embodiment has been described in order to facilitate understanding of the presently disclosed subject matter, and is not intended to limit the presently disclosed subject matter. It is a matter of course that the presently disclosed subject matter may be changed or improved without departing the spirit thereof, and includes equivalents thereof.

In the case where the controller 13 functions as the first determiner, it is not always necessary to determine the occurrence of inspiratory flow limitation based on the time period during which the amplitude of the secondary differential waveform S3 has a negative value. Alternatively, the controller 13 may be configured so as to, when the rate of the time period during which the amplitude of the secondary differential waveform S3 is smaller than a predetermined threshold, with respect to the duration time of the portion which is in the signal waveform S2, and which corresponds to expiration of the subject is equal to or larger than a predetermined value, determine that inspiratory flow limitation occurs. When the threshold is set with consideration of individual difference or the like, for example, the determination accuracy can be improved. When the detection is performed by using several thresholds which are set in a stepwise manner, the degree of intensity of inspiratory flow limitation can be determined.

It is not always necessary to dispose the pressure sensor 23 outside of the main unit of the monitoring apparatus 10. Alternatively, the pressure sensor may be configured so as to be incorporated in the monitoring apparatus 10 as a component which constitutes a part of the signal acquirer 11.

A respiration flow sensor or a temperature sensor may be used in place of the pressure sensor 23 as far as the alternative sensor can measure a signal waveform corresponding to the respiratory condition of the subject.

The signal waveform which is supplied to the signal acquirer 11, and which corresponds to the respiratory condition of the subject is not necessary to be the measurement waveform of the respiratory pressure of the subject. A configuration may be employed where the measurement waveform of the respiratory flow of the subject is directly supplied to the signal acquirer 11. In this case, the process of square root correction in the signal acquirer 11 is not required.

The device which guides the respiratory gas of the subject to the pressure sensor 23 or the monitoring apparatus 10 is not limited to the nasal cannula 21. In addition to or in place of this, a mask which covers the mouth of the subject may be used.

The display 14 is not always required to be disposed as a part of the monitoring apparatus 10. A configuration may be employed where a displaying device which is disposed outside the monitoring apparatus 10, and which is communicatably connected to the controller 13 functions as the display 14.

The manner of displaying the indexes indicating the presence of inspiratory flow limitation, that of the apnea/hypopnea condition, and the kind of the apnea/hypopnea condition in the display 14 is not limited to the example shown in FIG. 3. With respect to the presence of inspiratory flow limitation, for example, a bar index indicating a time zone in which inspiratory flow limitation frequently occurs may be displayed in addition to or in place of the display of the discrete dot indexes D. A configuration may be employed where at least one of the indexes indicating the presence of inspiratory flow limitation, that of the apnea/hypopnea condition, and the kind of the apnea/hypopnea condition is displayed together with the signal waveform S2.

According to an aspect of the presently disclosed subject matter, the presence of the inspiratory flow limitation can be uniformly determined without performing visual observation of the measurement waveform.

According to an aspect of the presently disclosed subject matter, it is possible to detect an upward convex portion which appears in a signal waveform corresponding to the respiratory pressure during inspiration, and which is large to some extent, and therefore it is possible to surely determine an occurrence of the inspiratory flow limitation. When the threshold is set with consideration of individual difference, the determination accuracy can be improved. When several thresholds are set in a stepwise manner, for example, the degree of intensity of the inspiratory flow limitation can be determined.

According to an aspect of the presently disclosed subject matter, waveforms in the start and end phases of inspiration which are hardly distinguished from those of normal inspiration can be eliminated from the analysis target, and the presence of the inspiratory flow limitation can be determined more surely.

According to an aspect of the presently disclosed subject matter, the apnea/hypopnea condition of the subject and the kind thereof can be uniformly determined without performing visual observation of the measurement waveform.

According to an aspect of the presently disclosed subject matter, the time zone where the inspiratory flow limitation occurs, that where an apnea/hypopnea condition occurs, and the kind of the apnea/hypopnea condition can be identified at a glance, and correct diagnosis which is not based on the subjectivity of the observer is enabled.

According to an aspect of the presently disclosed subject matter, since the pressure sensor which measures the respiratory pressure of the subject is provided, measurement can be performed more easily as compared with the case where the respiratory flow of the subject is measured.

According to an aspect of the presently disclosed subject matter, since a square root correction is performed on the measurement waveform corresponding to the respiratory pressure, an approximate value of the respiratory flow can be accurately obtained.

According to an aspect of the presently disclosed subject matter, it is not necessary to attach various kinds of sensors to the body, and therefore botheration and pain which may be felt by the subject can be reduced. Particularly, the nasal cannula is relatively light in weight, and therefore interference with sleep can be suppressed.

What is claimed is:

1. An apparatus for determining an inspiratory flow limitation, the apparatus comprising:
    a signal acquirer which is configured to acquire a signal waveform corresponding to a respiratory flow of a subject; and
    a controller configured to function as (i) a first determiner to identify start and end phases of inspiration of the subject based on a gradient of the signal waveform and to determine that inspiratory flow limitation occurs in the subject, (ii) an acquirer to acquire a gradient value of the signal waveform between a time t1 when an amplitude of the signal waveform changes from a positive value to a negative value and a time t4 when the amplitude of the signal waveform changes from a negative value to a positive value and (iii) a differential calculator to acquire a secondary differential waveform by performing secondary differentiation of the signal waveform,
    wherein the first determiner determines that inspiratory flow limitation occurs when the secondary differential waveform satisfies a predetermined condition in a portion of the signal waveform,
    wherein the portion of the signal waveform is a time period excluding the start and end phases of the inspiration of the subject, wherein
        the start phase is an amount of time between the time t1 and a time t2 when the gradient value of the signal waveform is less than a maximum gradient value and
        the end phase is an amount of time between the time t4 and a time t3 when the gradient value of the signal waveform is less than the maximum gradient value, wherein the predetermined condition, is satisfied when an amount of a time interval, characterized by the secondary differential waveform having a negative value, is equal to or larger than a predetermined value.

2. The apparatus according to claim 1, wherein the controller is further configured as:
   (iii) a second determiner to determine an apnea/hypopnea condition of the subject, based on an average value of an amplitude of the signal waveform in a predetermined past time period; and
   (iv) a third determiner which is configured to determine whether a kind of the apnea/hypopnea condition is obstructive or central, based on a presence of the inspiratory flow limitation which is determined by the first determiner and the apnea/hypopnea condition which is determined by the second determiner.

3. The apparatus according to claim 2, further comprising:
   a display which is configured to display the signal waveform; and
   a display controller which is configured to cause at least one of an index indicating the presence of the inspiratory flow limitation which is determined by the first determiner, an index indicating the apnea/hypopnea condition which is determined by the second determiner, and an index indicating the kind of the apnea/hypopnea condition which is determined by the third determiner, to be displayed on the display together with the signal waveform.

4. The apparatus according to claim 1, further comprising:
   a pressure sensor which is configured to measure a respiratory pressure of the subject,
   wherein the signal acquirer acquires the signal waveform based on a measurement waveform corresponding to the respiratory pressure which is output from the pressure sensor.

5. The apparatus according to claim 4, wherein the signal acquirer performs a square root correction on the measurement waveform to acquire the signal waveform.

6. The apparatus according to claim 1, further comprising:
   a nasal cannula which is to be attached to the subject,
   wherein the signal acquirer acquires the signal waveform based on a respiratory pressure which is introduced through the nasal cannula.

* * * * *